United States Patent [19]

Perboni

[11] Patent Number: 5,225,552
[45] Date of Patent: Jul. 6, 1993

[54] 4-CYCLOHEXENYL AZETIDINONE DERIVATIVES

[75] Inventor: Alcide Perboni, Verona, Italy

[73] Assignee: Glaxo SpA, Verona, Italy

[21] Appl. No.: 847,937

[22] Filed: Mar. 6, 1992

[30] Foreign Application Priority Data

Mar. 7, 1991 [GB] United Kingdom ............... 9104833

[51] Int. Cl.$^5$ ............... C07F 9/568; C07F 9/6561
[52] U.S. Cl. ............................. 540/200; 540/302
[58] Field of Search ........................ 540/200

[56] References Cited

U.S. PATENT DOCUMENTS 5,138,048  8/1992  Tamburini ................. 540/200

OTHER PUBLICATIONS

Adam et al., Chem. Ber., 124, 2361–2368, 1991.

Primary Examiner—Mark L. Berch
Attorney, Agent, or Firm—Bacon & Thomas

[57] ABSTRACT

Compounds of formula

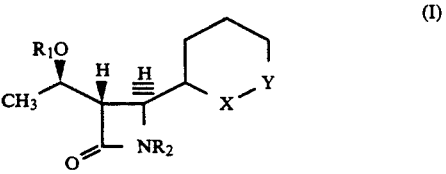

(I)

in which $R_1$ represents a hydrogen atom or a hydroxyl protecting group; $R_2$ represents a hydrogen atom or a trialkylsilyl group, and —X—Y— represents the epoxide group (A) or the alkene group (B).

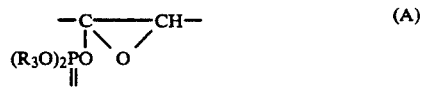

(A)

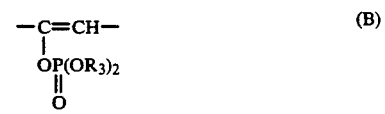

(B)

wherein $R_3$ represents a $C_{1-6}$alkyl group optionally substituted by halogen or an optionally substituted phenyl group, useful as intermediates in the preparation of antibacterially active compound.

19 Claims, No Drawings

4-CYCLOHEXENYL AZETIDINONE DERIVATIVES

This invention relates to novel heterocyclic compounds useful in the preparation of compounds having antibacterial activity, and to processes for their preparation.

Thus the present invention provides compounds of the general formula (I)

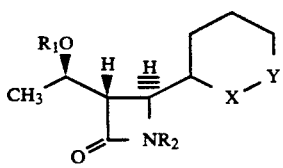

(I)

in which $R_1$ represents a hydrogen atom or a hydroxyl protecting group; $R_2$ represents a hydrogen atom or a trialkylsilyl group, and —X—Y— represents the epoxide group (A) or the alkene group (B).

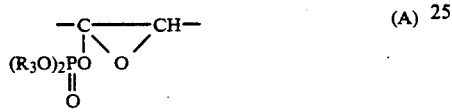

(A)

(B)

wherein $R_3$ represents a $C_{1-6}$ alkyl group optionally substituted by halogen or an optionally substituted phenyl group.

Suitable hydroxyl protecting groups $R_1$ include those which may be removed by hydrolysis under buffered conditions or under nonaqueous conditions.

When the group $OR_1$ is a protected hydroxyl group this is conveniently an ether or an acyloxy group. Examples of particularly suitable ethers include those in which $R_1$ is a hydrocarbylsilyl group such as trialkylsilyl, e.g. tri($C_{1-6}$alkyl)silyl such as trimethylsilyl or more especially t-butyldimethylsilyl. When the group $OR_1$ represents an acyloxy group then examples of suitable groups $R_1$ includes alkanoyl e.g. acetyl or pivaloyl; alkenoyl e.g. allylcarbonyl; aroyl e.g. p-nitrobenzoyl; alkoxycarbonyl e.g. t-butoxycarbonyl; haloalkoxycarbonyl e.g. 2,2,2-trichloroethoxycarbonyl, or 1,1,1-trichloro-2-methyl-2-propoxycarbonyl; aralkyloxycarbonyl e.g. benzyloxycarbonyl or p-nitrobenzyloxycarbonyl; or alkenyloxycarbonyl e.g. allyloxycarbonyl.

When $R_2$ represents a trialkylsilyl group this is preferably a tri($C_{1-6}$)alkylsilyl group such as trimethylsilyl or t-butyldimethylsilyl.

When $R_3$ represents $C_{1-6}$alkyl examples of suitable groups include methyl, ethyl, propyl, isopropyl, butyl and pentyl.

When $R_3$ represents a $C_{1-6}$alkyl group substituted by halogen the halogen may be fluorine, chlorine or bromine. Examples of suitable haloalkyl groups include mono, di and trichloroalkyl such as trichloroethyl.

When $R_3$ represents an optionally substituted phenyl group this may be for example a phenyl group optionally substituted by one or more groups selected from $C_{1-3}$alkyl e.g. methyl, halogen e.g. chlorine or alkoxy e.g. methoxy. For example $R_3$ may be phenyl, chlorophenyl or 3,5-dimethylphenyl.

Preferably $R_3$ is a group selected from methyl, ethyl, propropyl, isopropyl, butyl, pentyl, 2,2,2-trichloroethyl, phenyl, 2-chlorophenyl or 3,5-dimethyl phenyl.

The two groups $R_3$ may be the same or different.

In formula I the wedge shaped bond ◄ indicates that the bond is above the plane of the paper. The broken bond indicates that the bond is below the plane of the paper.

In addition to the fixed stereochemical arrangement as defined in formula (I) the molecule contains at least one further centre of asymmetry, and when X-Y is the epoxide group (A) there are also two additional centres of asymmetry. All stereoisomers including mixtures thereof arising from these additional asymmetric centres are within the scope of the compounds of formula (1). The specific stereoisomers of formula (I) may be represented by formulae (1a) to (1f).

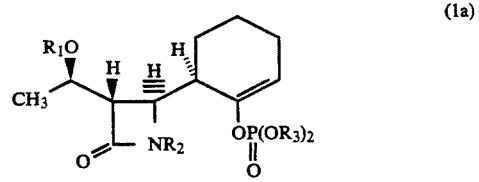

(1a)

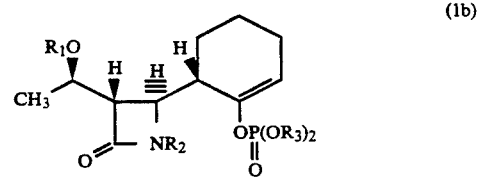

(1b)

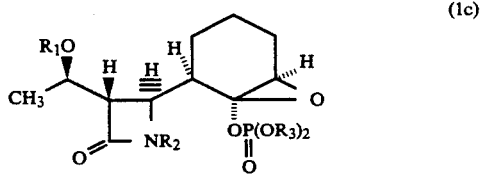

(1c)

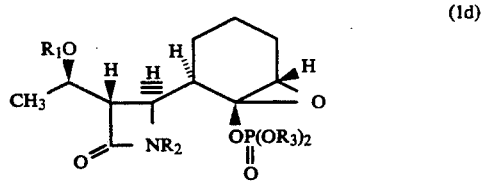

(1d)

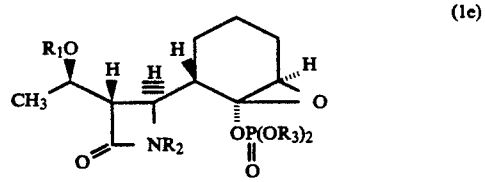

(1e)

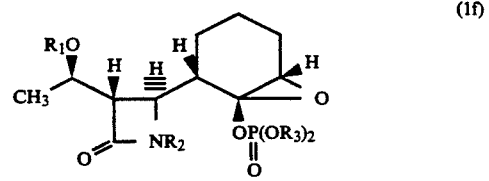

(1f)

A preferred class of compounds of formula (I) are the particular isomers as represented by formula (Ia) and (Ic).

Preferred compounds of formula (I) are those wherein $R_1$ represent a hydroxyl protecting group more particularly a trialkylsilyl group such as trimethylsilyl or t-butyldimethylsilyl.

A further preferred group of compounds of formula (I) are those wherein $R_2$ represent a hydrogen atom or a tri-$(C_{1-4})$alkyl group and in particular a t-butyldimethylsilyl or trimethylsilyl group.

A further preferred group of compounds of formula (I) are those wherein $R_3$ is a $C_{1-4}$alkyl group and most preferably both $R_3$ groups are the same e.g. ethyl.

A particular preferred class of compounds of formula (I) are the stereoisomers of formula (Ia) and (Ic) wherein $R_1$ represents a tri$(C_{1-4})$alkylsilyl group such as trimethylsilyl or t-butyldimethylsilyl; $R_2$ represents hydrogen, t-butyldimethylsilyl, or trimethylsilyl and $R_3$ represents $C_{1-4}$alkyl such as ethyl. More particularly for the compounds of formula (Ic) especially preferred compounds are those wherein $R_2$ represents a hydrogen atom.

The compound of formula (I) in which $R_1$ represents a hydroxyl protecting group and X-Y represent the epoxide group (A) may be prepared by epoxidation of the corresponding compound of formula (I) in which X-Y represents the alkene group B.

The epoxidation may conveniently be carried out by treating a compound of formula (I) wherein X-Y is the group B with a peracid. Suitable peracids include optionally substituted perbenzoic acids such as perbenzoic acid or meta chloroperbenzoic acid, peralkanoic acids such as peracetic acid and trifluoroperacetic acid. The reaction may be carried out in a solvent such as a halohydrocarbon e.g. dichloromethane and conveniently at a temperature within the range $-30°$ to $+30°$ C.

For the preparation of the epoxides as represented by formulae (Ic) and (Ie) the reaction is preferably carried out using the corresponding alkene formulae (Ia) or (Ib) in which $R_2$ represents hydrogen. For the preparation of epoxides as represented by formulae (Id) and (If) the epoxidation is preferably carried out using a cycloalkene of formula (Ia) or (Ib) wherein $R_2$ is a trialkylsilyl.

Compounds of formula (I) wherein $R_1$ is a hydroxyl protecting group and x represents the group s may be prepared treating the ketone (II) in which $R_4$ is a $C_{1-6}$alkyl group

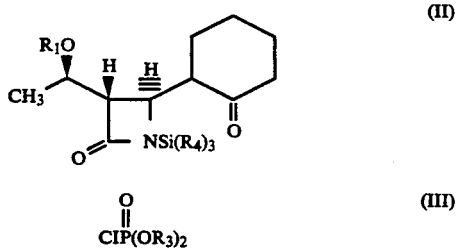

with a strong base such as a potassium or lithium bis(trimethylsilyl)amide) and then reacting the enolate ion thus formed with the chlorophosphate (III) followed by hydrolysis of the N-trialkylsilyl protecting group if desired.

Compounds of formula (I) wherein $R_2$ represents a hydrogen atom may be prepared from compounds of formula (I) wherein $R_2$ is a trialkylsilyl group by hydrolysis using conventional procedures for the removal of such groups. Thus for example compounds wherein $R_2$ is t-butyldimethylsilyl may be hydrolysed by reaction with potassium fluoride in methanol.

Compounds of formula (I) in which $R_1$ represents a hydrogen atom may be prepared from a compound in which $R_1$ represents a hydroxyl protecting group by the use of conventional procedures for the removal of such groups.

Compounds of formula (I) in which $R_1$ represents a hydroxyl protecting group, including those containing an alkenyl moiety, may be prepared from the compound of formula (I) in which $R_1$ represents a hydrogen atom using conventional procedures for preparing such protected hydroxyl functions.

In formulae (I) and (II) shown above when there is an asymmetric carbon atom and no specific configuration is shown then the formula includes all possible configurations.

Specific stereoisomers of the compounds of formula (I) as defined in formulae (Ia), (Ib), (Ic), (Id), (Ie) and (If) essentially free of the other stereoisomers may be prepared by using the general processes described above starting with the appropriate stereoisomer of formula (II) and the required substituent $R_2$.

The compounds of formula (I) are useful intermediates for the preparation of compounds having useful antibacterial activity. Thus the compounds of formula (I) may be used to prepare the antibacterial compounds described in EP-A-0416953A. For example the compounds (I) may be used to prepare compounds of formula (IV)

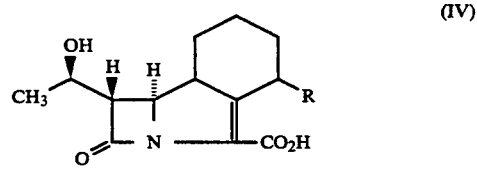

in which R is an amino group, for example methylamino, and salts thereof. These compounds exhibit a broad spectrum of antibacterial activity against a wide range of pathogenic microorganisms and have a very high resistance to all $\beta$-lactamases.

EP-A-0416953A teaches that compounds of formula (IV) may be readily prepared from compound (V)

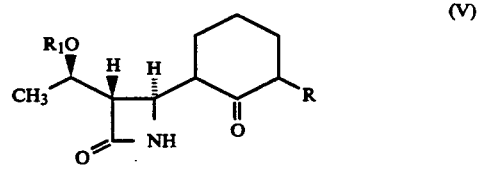

in which $R_1$ is a hydroxyl protecting group and R is a protected amino such as an allyloxycarbonyl protected amino group.

Compounds of formula (V) may be advantageously prepared from the compound of formula (I) wherein —X—Y is the epoxide group A by reaction with the appropriate amine e.g. methylamine, followed by reaction with allyl chloroformate in the presence of a tertiary base such as triethylamine.

In the above reactions the use of a specific stereoisomer of formula (I) as starting material will give a specific isomer of the compounds of formula (V) which may then be converted into a specific isomer of a compound of formula (IV). Thus the epoxide of formula (Ic) will give a compound of formula (IVa).

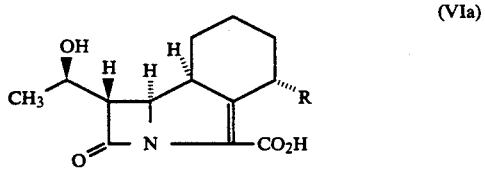

(VIa)

The compounds of formula (VIa) are particularly useful antibacterial agents and thus the compound of formula (Ic) represents a particularly preferred feature of the invention.

In order that the invention may be more fully understood the following examples are given by way of illustration only.

In the Preparations and Examples, unless otherwise stated:

Melting points (m.p.) were determined on a Gallenkamp m.p. apparatus and are uncorrected. All temperatures refer to °C.

Infrared spectra were measured in chloroform-$d_1$ solutions on a FT-IR instrument. Proton Magnetic Resonance (1H-NMR) spectra were recorded at 300 MHz as solutions in chloroform-$d_1$. Chemical shifts are reported in ppm downfield ($\delta$) from $Me_4Si$, used as an internal standard, and are assigned as singlets (s), doublets (d), doublet of doublets (dd) or multiplets (m).

Column chromatography was carried out over silica gel (Merck AG Darmstadt, Germany).

Solutions were dried over anhydrous sodium sulphate.

"Petrol" refers to petroleum ether, b.p. 40°–60° C.
Tlc refers to thin layer chromatography on silica plates.
Hplc refers to high performance liquid chromatograph.

INTERMEDIATE 1

(3S,4R)-1-(t-butyldimethylsilyl)-4-acetoxy-3[(R)-(T-butyldimethylsilyloxy)ethyl]azetidin-2-one To a stirred ice-cold solution of the (3s,4R)-4-acetoxy-3[(R)-(1-t-butyldimethylsilyloxy)ethyl]-2azetidinone (112 g) in dichloromethane (800 ml), t-butyldimethylchlorosilane (73 g) and triethylamine (80 ml) were added. The mixture was stirred at room temperature for 20 hr then washed with water (1 l) and brine (300 ml). The organic layer was dried and evaporated to give an oil (160 g) which was dissolved in a mixture of cyclohexane/ethyl acetate (95/5) (160 ml) and treated with silica gel (480g). The suspension was stirred for 15 min then filtered. The solid was washed with cyclohexane/ethyl acetate (95/5: 4.8l) and the solvent evaporated to give the title compound (110 g) as a pale yellow oil. (Rf=0.85 petrol/diethyl ether =2/1)

IR(CDCl$_3$)V$_{max}$ (cm$^{-1}$): 1747(c=O) H$^1$-NMR (CDCl$_3$) 6.14(d), 4.15(m), 3.07(dd), 2.03(s), 1.2(d), 0.9(s), 0.84(s), 0.22(s), 0.055(s), 0.35(s), 0.005(s)ppm.

INTERMEDIATE 2

(3S,4R)-1-(t-butyldimethylsily-3-[(R)-1-(t-butyldimethylsilyloxy)ethyl]-4-[2'-(1'-oxo-cyclohexyl)]azetidin-2-one Stannic chloride (35.4 ml) was added dropwise to stirred acetonitrile (400 ml) under nitrogen atmosphere at −4° C., a white solid formed together with white fumes which were eliminated by nitrogen flushing. The obtained suspension was allowed to rise to −10° C. then a solution of 1-trimethylsilyloxyoyclohexene (60.6 ml) and compound of Intermediate (1) (110 g) in acetonitrile (300 ml) was added in 10 minutes. The yellow solution was stirred at 0° C. for 10 min then poured into a stirred, ice-cold, mixture of a 10% aq solution of sodium hydroxide (1 l), diethyl ether (1 l) and ice (500 g). The organic layer was separated, washed again with sodium hydroxide (500 ml), then with a saturated solution of ammonium chloride, dried and evaporated to give a yellow solid (117.7 g). The solid was dissolved at 4° C. in isopropanol (300 ml) cooled to room temperature, water (300 ml) was added slowly under stirring to obtain a solid which was stirred at 0° C. for 30 min. The solid was filtered, washed with a 1 to 1 mixture of isopropanol/water (100 ml) and dried under vacuum at 40° C. for 15 hr to afford the title compound (76 g) as a mixture of 2'R and 2's isomers in a ratio of 70% to 30% (the ratio between the two isomers was determined by HPLC using hexane/ethanol (99/1) as eluant).

EXAMPLE 1

(3S,4R,6'R)-1-t-butyldimethylsilyl-3-[(R)-1-(t-butyldimethylsilyloxy)ethyl]-4-[6'-(1'-diethoxyphosphinyloxycyclohex-1'-ene]azetidin-2-one A 1M solution of lithium bis(trimethylsilyl)amide in hexane (9 ml) was added to tetrahydrofuran (15 ml), the mixture was cooled to −70° C. under nitrogen, then the intermediate 2 (1.9 g) dissolved in tetrahydrofuran (10 ml) was added over 10 min. The obtained solution was stirred for 45 min, then diethyl chlorophosphonate (1.4 ml) was added over 2 min. The reaction mixture was stirred for 30 min, allowed to warm to −20° C. then poured into a saturated ammonium chloride solution and the resulting mixture extracted with diethyl ether. The organic layer was washed with a 5% ice-cold solution of acetic acid, aqueous solution of sodium hydrogen carbonate and brine, dried and evaporated to give a yellow oil which was purified on silica gel (rf=0.65 diethyl ether) to afford the title compound (1.8 g) as a colourless oil

IR 1732(C=O), 1670(C=C)

NMR : 5.73(m), 4.2−4(m), 3.83(m), 3.02(dd), 2.68(m), 2.09(m), 1.79−1.45(m), 1.34(t), 1.25(d), 0;96(s), 0.88(s), 0.30(s), 0.20(s), 0.087(s) and 0.066(s).

EXAMPLE 2

(3S,4R,6'R)-3-[(R)-1-(t-butyldimethylsilyloxyl)ethyl-4-[6'-(1'-diethoxyphosphinyloxycyclohex-1'-ene]azetidin-2-one Example 1 (1 g) was dissolved at room temperature in methanol (25 ml) and treated with potassium fluoride (500 mg). The reaction mixture was stirred for 30 min. Then the solvent was partially evaporated under reduced pressure. The obtained thick suspension was poured into a saturated ammonium chloride solution and the resulting mixture extracted with diethyl ether. The organic layer was washed with brine, dried and evaporated to give the title compound (750 ml) as a pale yellow oil (rf=0.6 ethyl acetate).

IR : 1755(C=O), 1676(C=C)

NMR : 5.99(m), 5.69(m), 4.25-4.10(m), 4.06(dd), 3.04(dd), 2.57(m), 1.9-1.5(m), 1.33(t), 1.21(d), 0.87(s) and 0.076(s).

EXAMPLE 3

(3S,4R,6'R, 2'R, 1'S)-3-[(R)-1-(t-butyldimethylsilyloxy) ethyl-4-[6'-(1'-diethoxyphosphinyloxycyclohex-'2-ene oxide]azetidin-2-one Example 2 (700 mg) was dissovled in dichloromethane (25 ml) at 0° C. sodium hydrogen carbonate (250mg), and metachloroperbenzoic acid (700 mg) were added. The obtained suspension was stirred at 0° C. for 1 hr, at room temperatue for 1 hr then poured into an ice cold 3% aqueous sodium sulphite solution. The organic layer was separated and evaporated at 20° C. to give an oil which was dissolved in ethyl acetate and washed with a dilute ice-cold solution of sodium hydroxide, water and brine, dried and evaporated to give a yellow oil. The crude compound was purified on silica gel (rf=0.5 ethyl acetate) to afford the pure title compound (400 mg).

IR : 3416(NH), 1757(C—O)

NMR : 5.91(m), 4.25(m), 4.21(dd), 4.12(m), 3.79(d), 3.08(t), 2.49(m), 2.0—1.9(m), 1.8—1.7(m), 1.65—1.45(m), 1.45—1.3(m) 1.34(mn), 1.24(d), 0.88(s), 0.087(s) and 0.081(s).

EXAMPLE 4

(3S,4R)-3-((R)-1-(t-butyldimethylsilyloxy)ethyl)-4-((1'S,2'S,6'R)-2'-N-allyloxycarbonyl-N-methylamino)-1'-oxocyclohex-6'-yl)azetldin-2-one To a solution of Example 3 (49 g) of ethylacetate (500 ml) with potassium carbonate (213 g) at 0° under nitrogen was added methylamine (16 g, 40% water). The reaction mixture was stirred for 1 hour at 0° then the ethyl acetate was decanted and the residual solid was washed with ethyl acetate (100 ml). The organic solution was washed with water (3×600 ml) and brine (1×500 ml) dried, concentrated in vacuo to 500 ml and cooled to 0°. To the solution allyl chloroformate (17 ml) and triethylamine (22 ml) were added. The reaction mixture was stirred for 30 min at 0° then washed with a saturated aqueous solution of ammonium chloride (300 ml), water (2×500 ml), brine (300 ml) dried and evaporated in vacuo. The residue was purified by trituration at reflux in petroleum ether (250 ml) to obtain the title compound as a white powder (24.9 g; m.p. 159°-161° t.l.c. diethyl ether/ethylacetate 3/2 Rf=0.68).

IR $_{max}$ (CDCl$_3$) 3414, 1753, 1688 cm−1;

H$^1$NMR (300 Mhz CDCl$_3$): 6.2(bs), 5.9(m), 5.2(m), 4.6(m), 4.2(m), 4.04(m), 3.87(dd), 3.8(m), 3.17ldd), 2.86(s), 2.26(m), 1.8—1.2(m), 1.30(d), 0.89(s), 0.10(s), 0.09(s).

I claim:

1. Compounds of the formula (I)

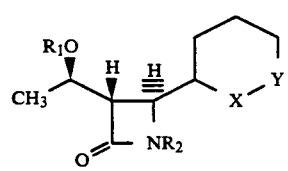

in which $R_1$ represents a hydrogen atom or a hydroxyl protecting group; $R_2$ represents a hydrogen atom or a trialkylsilyl group, and —X—Y— represents the epoxide group (A) or the alkene group (B):

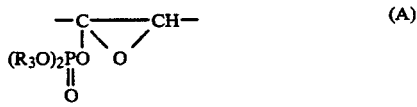

wherein $R_3$ represents a $C_{1-6}$alkyl group optionally substituted by halogen or a phenyl group optionally substituted by one or more groups selected from $C_{1-3}$ alkyl, halogen or alkoxy.

2. Compounds as claimed in claim 1 having the formula (1a)

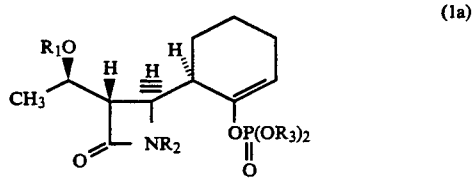

where $R_1$, $R_2$ and $R_3$ are as defined in claim 1.

3. Compounds as claimed in claim 1 having the formula (1c)

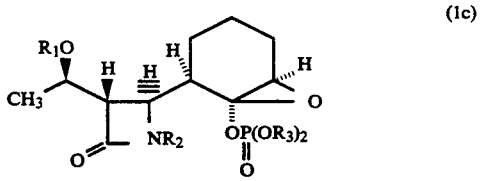

where $R_1$ and $R_3$ are as defined in claim 1 and $R_2$ is hydrogen.

4. Compounds as claimed in any of claim 1 wherein $R_1$ is trialkylsilyl.

5. Compounds as claimed in any of claim 1 wherein $R_1$ is t-butyldimethylsilyl.

6. Compounds as claimed in any of claim 1 wherein $R_2$ is hydrogen, trimethylsilyl or t-butyldimethylsilyl.

7. Compounds as claimed in any of claim 1 wherein $R_3$ is methyl, ethyl, propyl, isopropyl, butyl, pentyl, 2,2,2-trichloroethyl, phenyl, 2-chlorophenyl, or 3,5-dimethylphenyl, and the two $R_3$ groups may be the same or different.

8. Compounds as claimed in any of claim 1 wherein $R_3$ is $C_{1-4}$alkyl.

9. Compounds as claimed in any of claim 1 wherein $R_3$ is ethyl.

10. Compounds as claimed in claim 3 wherein $R_3$ is $C_{1-4}$ alkyl.

11. Compounds as claimed in claim 2 wherein $R_1$ is trialkylsilyl.

12. Compounds as claimed in claim 3 wherein $R_1$ is trialkylsilyl.

13. Compounds as claimed in claim 2 wherein $R_1$ is t-butyldimethylsilyl.

14. Compounds as claimed in claim 3 wherein $R_1$ is t-butyldimethylsilyl.

15. Compounds as claimed in claim 2 wherein $R_2$ is hydrogen, trimethylsilyl or t-butyldimethylsilyl.

16. Compounds as claimed in claim 3 wherein $R_2$ is hydrogen, trimethylsilyl or t-butyldimethylsilyl.

17. Compounds as claimed in claim 2 wherein $R_3$ is methyl, ethyl, propyl, isopropyl, butyl, pentyl, 2,2,2-trichloroethyl, phenyl, 2-chlorophenyl, or 3-5-dimethylphenyl and the two $R_3$ groups may be the same or different.

18. Compounds as claimed in claim 3 wherein $R_3$ is methyl, ethyl, propyl, isopropyl, butyl, pentyl, 2,2,2-trichloroethyl, phenyl, 2-chlorophenyl, or 3-5-dimethylphenyl and the two $R_3$ groups may be the same or different.

19. Compounds as claimed in claim 2 wherein $R_3$ is $C_{1-4}$-alkyl.

* * * * *